(12) United States Patent
Delanely, Jr. et al.

(10) Patent No.: US 10,328,272 B2
(45) Date of Patent: Jun. 25, 2019

(54) RETRIEVABILITY FOR IMPLANTABLE MEDICAL DEVICES

(71) Applicant: CARDIAC PACEMAKERS, INC., St. Paul, MN (US)

(72) Inventors: Joseph Thomas Delanely, Jr., Minneapolis, MN (US); Michael J. Kane, Roseville, MN (US); Benjamin J. Haasl, Forest Lake, MN (US); Danielle Frankson, Dayton, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 4 days.

(21) Appl. No.: 15/589,642

(22) Filed: May 8, 2017

(65) Prior Publication Data

US 2017/0326373 A1 Nov. 16, 2017

Related U.S. Application Data

(60) Provisional application No. 62/334,237, filed on May 10, 2016.

(51) Int. Cl.
| | |
|---|---|
| *A61N 1/362* | (2006.01) |
| *A61N 1/375* | (2006.01) |
| *A61N 1/05* | (2006.01) |
| *A61L 31/02* | (2006.01) |
| *A61L 31/10* | (2006.01) |
| *A61L 31/14* | (2006.01) |

(52) U.S. Cl.
CPC .......... *A61N 1/3756* (2013.01); *A61L 31/022* (2013.01); *A61L 31/10* (2013.01); *A61L 31/14* (2013.01); *A61N 1/0573* (2013.01); *A61N 1/362* (2013.01); *A61N 1/37512* (2017.08); *A61L 2400/18* (2013.01)

(58) Field of Classification Search
CPC ...................................................... A61N 1/362
See application file for complete search history.

(56) References Cited

U.S. PATENT DOCUMENTS

| | | |
|---|---|---|
| 3,835,864 A | 9/1974 | Rasor et al. |
| 3,943,936 A | 3/1976 | Rasor et al. |
| (Continued) | | |

FOREIGN PATENT DOCUMENTS

| | | |
|---|---|---|
| AU | 2008279789 B2 | 10/2011 |
| AU | 2008329620 B2 | 5/2014 |
| (Continued) | | |

OTHER PUBLICATIONS

US 8,886,318 B2, 11/2014, Jacobson et al. (withdrawn)
(Continued)

*Primary Examiner* — Benjamin J Packard
(74) *Attorney, Agent, or Firm* — Seager, Tufte & Wickhem LLP

(57) ABSTRACT

An implantable medical device (IMD) may include an outer housing having a titanium outer surface, the titanium outer surface including a plurality of titanium atoms. A tissue growth-inhibiting layer may extend over the titanium outer surface. In some cases, the tissue growth-inhibiting layer may include a plurality of polyethylene glycol molecules, at least some of the plurality of polyethylene glycol molecules covalently bonded via an ether bond to one of the plurality of titanium atoms.

19 Claims, 6 Drawing Sheets

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |

(56) References Cited

U.S. PATENT DOCUMENTS

| | | | |
|---|---|---|---|
| 6,144,879 A | 11/2000 | Gray | |
| 6,162,195 A | 12/2000 | Igo et al. | |
| 6,164,284 A | 12/2000 | Schulman et al. | |
| 6,167,310 A | 12/2000 | Grevious | |
| 6,201,993 B1 | 3/2001 | Kruse et al. | |
| 6,208,894 B1 | 3/2001 | Schulman et al. | |
| 6,211,799 B1 | 4/2001 | Post et al. | |
| 6,221,011 B1 | 4/2001 | Bardy | |
| 6,240,316 B1 | 5/2001 | Richmond et al. | |
| 6,240,317 B1 | 5/2001 | Villaseca et al. | |
| 6,256,534 B1 | 7/2001 | Dahl | |
| 6,259,947 B1 | 7/2001 | Olson et al. | |
| 6,266,558 B1 | 7/2001 | Gozani et al. | |
| 6,266,567 B1 | 7/2001 | Ishikawa et al. | |
| 6,270,457 B1 | 8/2001 | Bardy | |
| 6,272,377 B1 | 8/2001 | Sweeney et al. | |
| 6,273,856 B1 | 8/2001 | Sun et al. | |
| 6,277,072 B1 | 8/2001 | Bardy | |
| 6,280,380 B1 | 8/2001 | Bardy | |
| 6,285,907 B1 | 9/2001 | Kramer et al. | |
| 6,292,698 B1 | 9/2001 | Duffin et al. | |
| 6,295,473 B1 | 9/2001 | Rosar | |
| 6,297,943 B1 | 10/2001 | Carson | |
| 6,298,271 B1 | 10/2001 | Weijand | |
| 6,307,751 B1 | 10/2001 | Bodony et al. | |
| 6,312,378 B1 | 11/2001 | Bardy | |
| 6,315,721 B2 | 11/2001 | Schulman et al. | |
| 6,336,903 B1 | 1/2002 | Bardy | |
| 6,345,202 B2 | 2/2002 | Richmond et al. | |
| 6,351,667 B1 | 2/2002 | Godie | |
| 6,351,669 B1 | 2/2002 | Hartley et al. | |
| 6,353,759 B1 | 3/2002 | Hartley et al. | |
| 6,358,203 B2 | 3/2002 | Bardy | |
| 6,361,780 B1 | 3/2002 | Ley et al. | |
| 6,368,284 B1 | 4/2002 | Bardy | |
| 6,371,922 B1 | 4/2002 | Baumann et al. | |
| 6,398,728 B1 | 6/2002 | Bardy | |
| 6,400,982 B2 | 6/2002 | Sweeney et al. | |
| 6,400,990 B1 | 6/2002 | Silvian | |
| 6,408,208 B1 | 6/2002 | Sun | |
| 6,409,674 B1 | 6/2002 | Brockway et al. | |
| 6,411,848 B2 | 6/2002 | Kramer et al. | |
| 6,424,865 B1 | 7/2002 | Ding | |
| 6,434,429 B1 | 8/2002 | Kraus et al. | |
| 6,436,481 B1 * | 8/2002 | Chabrecek | A61L 27/34 427/488 |
| 6,438,410 B2 | 8/2002 | Hsu et al. | |
| 6,438,417 B1 | 8/2002 | Rockwell et al. | |
| 6,438,421 B1 | 8/2002 | Stahmann et al. | |
| 6,440,066 B1 | 8/2002 | Bardy | |
| 6,441,747 B1 | 8/2002 | Khair et al. | |
| 6,442,426 B1 | 8/2002 | Kroll | |
| 6,442,432 B2 | 8/2002 | Lee | |
| 6,443,891 B1 | 9/2002 | Grevious | |
| 6,445,953 B1 | 9/2002 | Bulkes et al. | |
| 6,453,200 B1 | 9/2002 | Koslar | |
| 6,459,929 B1 | 10/2002 | Hopper et al. | |
| 6,470,215 B1 | 10/2002 | Kraus et al. | |
| 6,471,645 B1 | 10/2002 | Warkentin et al. | |
| 6,480,745 B2 | 11/2002 | Nelson et al. | |
| 6,487,443 B2 | 11/2002 | Olson et al. | |
| 6,490,487 B1 | 12/2002 | Kraus et al. | |
| 6,498,951 B1 | 12/2002 | Larson et al. | |
| 6,507,755 B1 | 1/2003 | Gozani et al. | |
| 6,507,759 B1 | 1/2003 | Prutchi et al. | |
| 6,512,940 B1 | 1/2003 | Brabec et al. | |
| 6,522,915 B1 | 2/2003 | Ceballos et al. | |
| 6,526,311 B2 | 2/2003 | Begemann | |
| 6,539,253 B2 | 3/2003 | Thompson et al. | |
| 6,542,775 B2 | 4/2003 | Ding et al. | |
| 6,553,258 B2 | 4/2003 | Stahmann et al. | |
| 6,561,975 B1 | 5/2003 | Pool et al. | |
| 6,564,807 B1 | 5/2003 | Schulman et al. | |
| 6,574,506 B2 | 6/2003 | Kramer et al. | |
| 6,584,351 B1 | 6/2003 | Ekwall | |
| 6,584,352 B2 | 6/2003 | Combs et al. | |
| 6,597,948 B1 | 7/2003 | Rockwell et al. | |
| 6,597,951 B2 | 7/2003 | Kramer et al. | |
| 6,622,046 B2 | 9/2003 | Fraley et al. | |
| 6,628,985 B2 | 9/2003 | Sweeney et al. | |
| 6,647,292 B1 | 11/2003 | Bardy et al. | |
| 6,666,844 B1 | 12/2003 | Igo et al. | |
| 6,689,117 B2 | 2/2004 | Sweeney et al. | |
| 6,690,959 B2 | 2/2004 | Thompson | |
| 6,694,189 B2 | 2/2004 | Begemann | |
| 6,704,602 B2 | 3/2004 | Berg et al. | |
| 6,718,212 B2 | 4/2004 | Parry et al. | |
| 6,721,597 B1 | 4/2004 | Bardy et al. | |
| 6,738,670 B1 | 5/2004 | Almendinger et al. | |
| 6,746,797 B2 | 6/2004 | Benson et al. | |
| 6,749,566 B2 | 6/2004 | Russ | |
| 6,758,810 B2 | 7/2004 | Lebel et al. | |
| 6,763,269 B2 | 7/2004 | Cox | |
| 6,778,860 B2 | 8/2004 | Ostroff et al. | |
| 6,788,971 B1 | 9/2004 | Sloman et al. | |
| 6,788,974 B2 | 9/2004 | Bardy et al. | |
| 6,804,558 B2 | 10/2004 | Haller et al. | |
| 6,807,442 B1 | 10/2004 | Myklebust et al. | |
| 6,847,844 B2 | 1/2005 | Sun et al. | |
| 6,871,095 B2 | 3/2005 | Stahmann et al. | |
| 6,878,112 B2 | 4/2005 | Linberg et al. | |
| 6,885,889 B2 | 4/2005 | Chinchoy | |
| 6,892,094 B2 | 5/2005 | Ousdigian et al. | |
| 6,897,788 B2 | 5/2005 | Khair et al. | |
| 6,904,315 B2 | 6/2005 | Panken et al. | |
| 6,922,592 B2 | 7/2005 | Thompson et al. | |
| 6,931,282 B2 | 8/2005 | Esler | |
| 6,934,585 B1 | 8/2005 | Schloss et al. | |
| 6,957,107 B2 | 10/2005 | Rogers et al. | |
| 6,978,176 B2 | 12/2005 | Lattouf | |
| 6,985,773 B2 | 1/2006 | Von Arx et al. | |
| 6,990,375 B2 | 1/2006 | Kloss et al. | |
| 7,001,366 B2 | 2/2006 | Ballard | |
| 7,003,350 B2 | 2/2006 | Denker et al. | |
| 7,006,864 B2 | 2/2006 | Echt et al. | |
| 7,013,178 B2 | 3/2006 | Reinke et al. | |
| 7,027,871 B2 | 4/2006 | Burnes et al. | |
| 7,050,849 B2 | 5/2006 | Echt et al. | |
| 7,060,031 B2 | 6/2006 | Webb et al. | |
| 7,063,693 B2 | 6/2006 | Guenst | |
| 7,082,336 B2 | 7/2006 | Ransbury et al. | |
| 7,085,606 B2 | 8/2006 | Flach et al. | |
| 7,092,758 B2 | 8/2006 | Sun et al. | |
| 7,110,824 B2 | 9/2006 | Amundson et al. | |
| 7,120,504 B2 | 10/2006 | Osypka | |
| 7,130,681 B2 | 10/2006 | Gebhardt et al. | |
| 7,139,613 B2 | 11/2006 | Reinke et al. | |
| 7,142,912 B2 | 11/2006 | Wagner et al. | |
| 7,146,225 B2 | 12/2006 | Guenst et al. | |
| 7,146,226 B2 | 12/2006 | Lau et al. | |
| 7,149,581 B2 | 12/2006 | Goedeke | |
| 7,149,588 B2 | 12/2006 | Lau et al. | |
| 7,158,839 B2 | 1/2007 | Lau | |
| 7,162,307 B2 | 1/2007 | Patrias | |
| 7,164,952 B2 | 1/2007 | Lau et al. | |
| 7,177,700 B1 | 2/2007 | Cox | |
| 7,181,505 B2 | 2/2007 | Haller et al. | |
| 7,184,830 B2 | 2/2007 | Echt et al. | |
| 7,186,214 B2 | 3/2007 | Ness | |
| 7,191,015 B2 | 3/2007 | Lamson et al. | |
| 7,200,437 B1 | 4/2007 | Nabutovsky et al. | |
| 7,200,439 B2 | 4/2007 | Zdeblick et al. | |
| 7,206,423 B1 | 4/2007 | Feng et al. | |
| 7,209,785 B2 | 4/2007 | Kim et al. | |
| 7,209,790 B2 | 4/2007 | Thompson et al. | |
| 7,211,884 B1 | 5/2007 | Davis et al. | |
| 7,212,871 B1 | 5/2007 | Morgan | |
| 7,226,440 B2 | 6/2007 | Gelfand et al. | |
| 7,228,183 B2 | 6/2007 | Sun et al. | |
| 7,236,821 B2 | 6/2007 | Cates et al. | |
| 7,236,829 B1 | 6/2007 | Farazi et al. | |
| 7,254,448 B2 | 8/2007 | Almendinger et al. | |
| 7,260,436 B2 | 8/2007 | Kilgore et al. | |
| 7,270,669 B1 | 9/2007 | Sra | |

(56) References Cited

U.S. PATENT DOCUMENTS

| | | |
|---|---|---|
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |

(56) References Cited

U.S. PATENT DOCUMENTS

| | | |
|---|---|---|
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Mates |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bomzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |

(56) References Cited

U.S. PATENT DOCUMENTS

| | | |
|---|---|---|
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0116034 A1* | 8/2002 | Miller ............... A61N 1/056 607/33 |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |

(56) References Cited

U.S. PATENT DOCUMENTS

| | | |
|---|---|---|
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |

(56) References Cited

U.S. PATENT DOCUMENTS

| | | |
|---|---|---|
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bomzin et al. |
| 2013/0110192 A1 | 5/2013 | Tran et al. |
| 2013/0110219 A1 | 5/2013 | Bomzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bomzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025608 A1 | 1/2015 | Delaney, Jr. et al. |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |

(56) References Cited

U.S. PATENT DOCUMENTS

| | | |
|---|---|---|
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishier et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 2662113 A2 | 11/2013 |
| EP | 1948296 B1 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A2 | 1/2005 |
| WO | 2005042089 A1 | 5/2005 |
| WO | 2006065394 A1 | 6/2006 |
| WO | 2006086435 A2 | 8/2006 |
| WO | 2006113659 A1 | 10/2006 |
| WO | 2006124833 A2 | 11/2006 |
| WO | 2007075974 A2 | 7/2007 |
| WO | 2009006531 A1 | 1/2009 |
| WO | 2012054102 A1 | 4/2012 |
| WO | 2012082755 A1 | 6/2012 |
| WO | 2013080038 A2 | 6/2013 |
| WO | 2013098644 A2 | 7/2013 |
| WO | 2013184787 A1 | 12/2013 |
| WO | 2014120769 A1 | 8/2014 |

OTHER PUBLICATIONS

"Instructions for Use System 1, Leadless Cardiac Pacemaker (LCP) and Delivery Catheter," Nanostim Leadless Pacemakers, pp. 1-28, 2013.

Alcantar, "Polyethylene glycol-coated biocompatible surfaces", Chemical Engineering Department and Materials Department, University of California, Jan. 10, 2000, pp. 343-351, Santa Barbara, California.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering,vol. 60(8): 2067-2079, 2013.

Spickler et al., "Totally Self-Contained Intracardiac Pacemaker," Journal of Electrocardiology, vol. 3(384): 324-331, 1970.

Wegmüller, "Intra-Body Communication for Biomedical Sensor Networks," Diss. ETH, No. 17323, 1-173, 2007.

\* cited by examiner

RETRIEVABILITY FOR IMPLANTABLE MEDICAL DEVICES

CROSS REFERENCE TO RELATED APPLICATIONS

This application claims the benefit of U.S. Provisional Patent Application Ser. No. 62/334,237 filed on May 10, 2016, the disclosure of which is incorporated herein by reference.

TECHNICAL FIELD

The disclosure relates generally to implantable medical devices, and more particularly to ways of improving extractability of chronically implanted medical devices.

BACKGROUND

Cardiac pacemakers such as leadless cardiac pacemakers are used to sense and pace hearts that are susceptible to a variety of incorrect heart rhythms, including but not limited to bradycardia, which is a slow heart rate, and tachycardia, which is a high heart rate. In some cases, there may be a desire to remove a previously implanted leadless cardiac pacemaker. Since these devices are designed for long life, in many cases substantial tissue growth (e.g. endothelialization) around and even over the leadless cardiac pacemaker may occur, particularly with chronically (long-term) implanted devices. Tissue growth can complicate removal of the implanted device. Accordingly, there is a desire to provide implantable devices that are easier to extract, even when chronically implanted.

SUMMARY

The disclosure is directed to implantable medical devices that may be configured to be easier to extract. In some cases, implantable medical devices may, for example, be configured to reduce or even eliminate tissue growth over the implantable medical device such that there is less holding the implantable medical device in place and thus less resistance to removal. In some instances, at least certain portions of the implantable medical device such as, for example, a retrieval feature, may be configured to prevent tissue growth around and over the retrieval feature such that the retrieval feature may easily be grasped by an extraction device.

In an example of the disclosure, an implantable medical device (IMD) includes an outer housing having a titanium outer surface including a plurality of titanium atoms. A tissue growth-inhibiting layer may extend over the titanium outer surface and may, for example, include a plurality of polyethylene glycol molecules, at least some of which are covalently bonded via an ether bond to one of the plurality of titanium atoms.

Alternatively or additionally to any of the embodiments above, the tissue growth-inhibiting layer is formed by hydroxylating at least some of the plurality of titanium atoms and covalently bonding a plurality of hydroxyl-terminated polyethylene glycol molecules to the hydroxylated titanium atoms with a concomitant loss of water molecules.

Alternatively or additionally to any of the embodiments above, the titanium outer surface includes an electrically active surface.

Alternatively or additionally to any of the embodiments above, the IMD further includes an electrically insulating layer disposed over a first portion of the outer housing and the electrically active surface comprises a second portion of the outer housing without the electrically insulating layer.

Alternatively or additionally to any of the embodiments above, the tissue growth-inhibiting layer extends over at least a portion of the electrically active surface.

Alternatively or additionally to any of the embodiments above, the titanium outer surface includes a retrieval feature.

Alternatively or additionally to any of the embodiments above, the tissue growth-inhibiting layer extends over at least a portion of the retrieval feature.

Alternatively or additionally to any of the embodiments above, the tissue growth-inhibiting layer exhibits hydrolytic stability in the presence of water.

Alternatively or additionally to any of the embodiments above, the tissue growth-inhibiting layer is water-swellable.

In another example of the disclosure, a leadless cardiac pacemaker (LCP) configured for removal after having been chronically implanted includes an outer housing extending from a proximal end to a distal end, a fixation element extending distally from the distal end and a retrieval feature extending proximally from the proximal end. At least a portion of the LCP includes a titanium outer surface. A tissue growth-inhibiting layer extends over at least a portion of the titanium outer surface, the tissue growth-inhibiting layer comprising a plurality of polyethylene glycol molecules each covalently bonded to titanium atoms within the titanium outer surface.

Alternatively or additionally to any of the embodiments above, the LCP further includes a titanium electrode disposed relative to the outer housing.

Alternatively or additionally to any of the embodiments above, the tissue growth-inhibiting layer extends over at least a portion of the titanium electrode.

Alternatively or additionally to any of the embodiments above, the retrieval feature includes the titanium outer surface, and the tissue growth-inhibiting layer extends over at least a portion of the retrieval feature.

Alternatively or additionally to any of the embodiments above, the outer housing includes the titanium outer surface, and the tissue growth-inhibiting layer extends over at least a portion of the outer housing.

In another example of the disclosure, a method of instilling tissue growth resistance to at least a portion of an implantable medical device (IMD) having a titanium outer surface includes subjecting the titanium outer surface to a plasma treatment to provide hydroxyl groups on the titanium outer surface, the hydroxyl groups covalently bonded to titanium atoms within the titanium outer surface. The hydroxyl groups on the titanium outer surface may be contacted with hydroxyl-terminated polyethylene glycol molecules. The hydroxyl-terminated polyethylene glycol molecules covalently bond with the hydroxyl groups on the titanium outer surface with a concomitant loss of water molecules.

Alternatively or additionally to any of the embodiments above, contacting the hydroxyl groups on the titanium outer surface with hydroxyl-terminated polyethylene glycol molecules takes place within about one hour or less of subjecting the titanium outer surface to a plasma treatment to provide hydroxyl groups on the titanium outer surface.

Alternatively or additionally to any of the embodiments above, subjecting the titanium outer surface to a plasma treatment to provide hydroxyl groups on the titanium outer surface includes a water plasma treatment.

Alternatively or additionally to any of the embodiments above, subjecting the titanium outer surface to a plasma treatment to provide hydroxyl groups on the titanium outer surface includes an $O_2$ plasma treatment.

Alternatively or additionally to any of the embodiments above, the IMD is a leadless cardiac pacemaker (LCP).

Alternatively or additionally to any of the embodiments above, the covalently bonded polyethylene glycol molecules inhibit tissue growth.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE FIGURES

The disclosure may be more completely understood in consideration of the following detailed description in connection with the accompanying drawings, in which.

Figure 1:
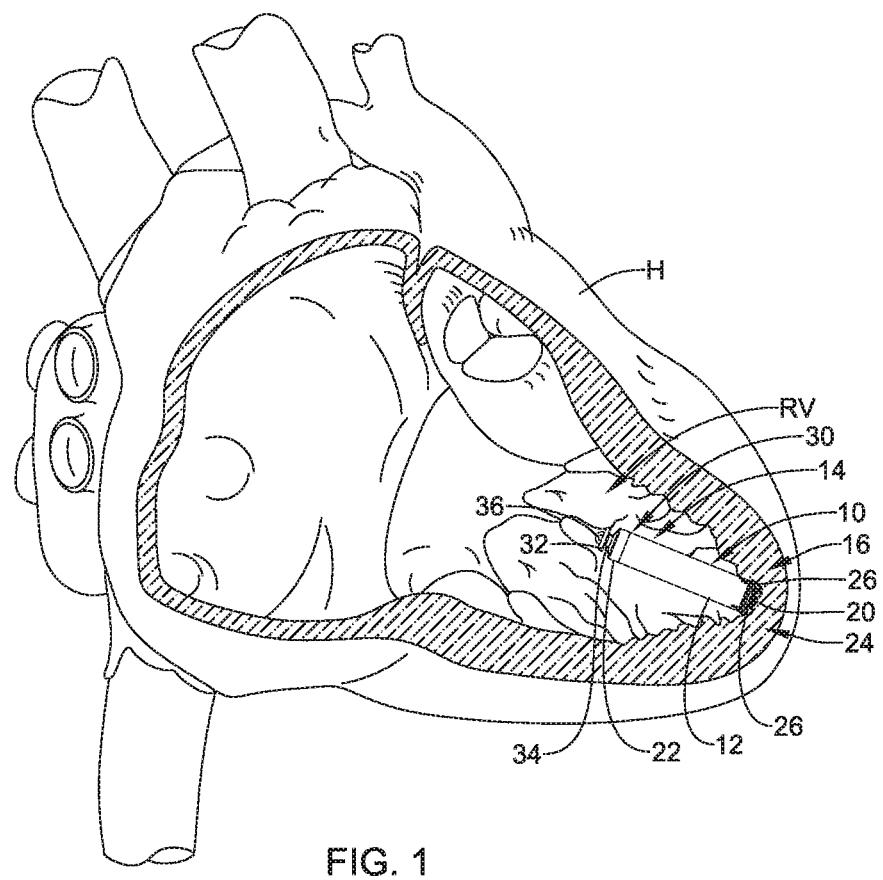
FIG. 1 is a partial cut away plan view of an example leadless pacing device implanted within a heart.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers may include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules that may, for example, be fixed to an intracardiac implant site in a cardiac chamber. In some cases, the small capsule may include bipolar pacing/sensing electrodes, a power source (e.g. a battery), and associated electrical circuitry for controlling the pacing/sensing electrodes, and thus may provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle.

While a leadless cardiac pacemaker is used as an example implantable medical device, the disclosure may be applied to any suitable implantable medical device including, for example, neuro-stimulators, diagnostic devices including those that do not deliver therapy, and/or any other suitable implantable medical device as desired.

Figure 2:
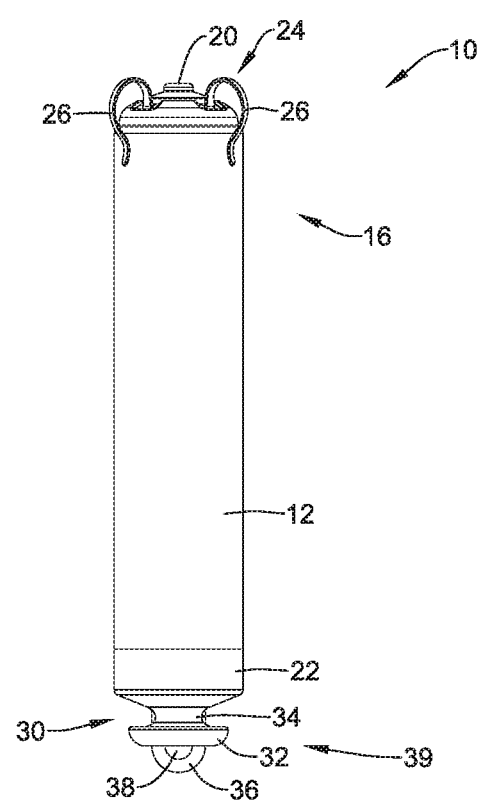
FIG. 2 is a side elevation view of an example implantable LCP device.

FIG. 1 illustrates an example implantable leadless cardiac pacing device 10 (e.g., a leadless pacemaker) implanted in a chamber of a heart H, such as the right ventricle RV. A side elevation view of the illustrative implantable medical device (IMD) 10 is shown in FIG. 2. The implantable device 10 may include a shell or housing 12 having a proximal end 14 and a distal end 16. In some instances, the IMD 10 may include a first electrode 20 positioned adjacent to the distal end 16 of the housing 12, and a second electrode 22 positioned adjacent to the proximal end 14 of the housing 12. In some cases, the housing 12 may include a conductive material and may be insulated at least a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be configured to be positioned against the cardiac tissue of the heart H or may otherwise contact the cardiac tissue of the heart H while the second electrode 22 may be spaced away from the first electrode 20, and thus spaced away from the cardiac tissue.

The illustrative IMD 10 may include a pulse generator (e.g., electrical circuitry) and a power source (e.g., a battery) within the housing 12 to provide electrical signals to the electrodes 20, 22 and thus control the pacing/sensing electrodes 20, 22. In some cases, electrical communication between the pulse generator and the electrodes 20, 22 may provide electrical stimulation to heart tissue and/or sense a physiological condition.

The IMD 10 may include a fixation mechanism 24 proximate the distal end 16 of the housing 12 configured to attach the IMD 10 to a tissue wall of the heart H, or otherwise anchor the IMD 10 to the anatomy of the patient. As shown in FIG. 1, in some instances, the fixation mechanism 24 may include one or more, or a plurality of hooks or tines 26 anchored into the cardiac tissue of the heart H to attach the IMD 10 to a tissue wall. In other cases, the fixation mechanism 24 may include one or more, or a plurality of passive tines, configured to entangle with trabeculae within the chamber of the heart H and/or a helical fixation anchor configured to be screwed into a tissue wall to anchor the IMD 10 to the heart H. These are just some examples.

The IMD 10 may include a docking member 30 proximate the proximal end 14 of the housing 12 configured to facilitate delivery and/or retrieval of the IMD 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the IMD 10 which is greater than a radial dimension of the neck portion 34 from the longitudinal axis of the IMD 10. In some cases, the docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g. looped) through the opening 38. The docking member 30 may be configured to facilitate delivery of the IMD 10 to the intracardiac site and/or retrieval of the IMD 10 from the intracardiac site. FIG. 2 shows one example docking member configuration. However, it is contemplated that any suitable docking member configuration may be used, as desired.

In some cases, the docking member 30, or at least a portion thereof, may be considered as providing a retrieval feature generally shown at 39 that may subsequently be grasped in order to retrieve the IMD 10 subsequent to implantation. The retrieval feature 39 may be grasped, for example, by a variety of different devices, such as but not limited to a retrieval loop, forceps and the like. In some cases, retrieval of a chronically implanted IMD 10, meaning that the IMD 10 has been in place within the anatomy for a period of time ranging from several months to multiple years, may be complicated by tissue ingrowth around part or even all of the IMD 10, including the retrieval feature 39. In some cases, it may be useful to cut through or otherwise remove at least some of the tissue ingrowth prior to actually retrieving the IMD 10.

In some cases, it may be beneficial to reduce or even prevent tissue ingrowth on or around part or even all of the IMD 10. In some cases, the IMD 10 or at least portions of the IMD 10 may be formed of titanium or include an outer surface of titanium. In many cases, titanium may be used to form the outer housing 12 since titanium is a biocompatible metal. In some instances, the first electrode 20 and/or the second electrode 22 may also be formed of titanium. While a variety of coatings are known for inhibiting tissue ingrowth on and about an implanted object, in some cases polyethylene glycol, or PEG, may be used. In general terms, polyethylene glycol is a polymer formed by an interaction of ethylene oxide with water, ethylene glycol, or ethylene glycol oligomers. Polyethylene glycol is generically shown by a Structure 1, where n is an integer that varies in accordance with polymer size:

Structure 1

A variety of different polyethylene glycol polymers are commonly used, and are applicable herein. In many cases, a polyethylene glycol polymer may be referred to as xxx PEG, where xxx refers to an approximate molecular weight. For example, 400 PEG 400 has the chemical formula $C_{2n}H_{4n+2}O_{n+1}$, where n varies from about 8.2 to 9.1 and has a molecular weight ranging from 380 g/mol to 420 g/mol. 400 PEG is a liquid at room temperature (melting point of 4 to 8° C.). Larger polyethylene glycol polymers may be solid at room temperature. For example, 3350 PEG is a solid at room temperature. Polyethylene glycol typically forms hydrogels in aqueous environments due to its high hydrophilicity. In some cases, adding a polyethylene glycol layer or coating to an implantable medical device such as the IMD 10 may inhibit tissue ingrowth without negatively impacting electrical properties of electrodes on the IMD 10.

Figure 3:
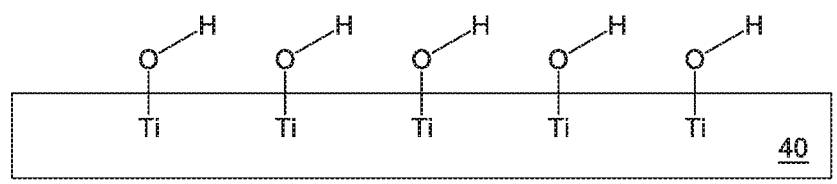
FIG. 3 is a schematic view of a titanium surface representative of a portion of an implantable medical device (IMD), shown after hydroxylation.

In some cases, polyethylene glycol may be added to some metal surfaces such as titanium without first providing one or more intervening coatings or tie layers. In some cases, it has surprisingly been determined that a titanium surface may be subjected to a plasma treatment such as a water plasma treatment or an $O_2$ plasma treatment. FIG. 3 is a schematic illustration of a titanium surface 40 after a plasma treatment. The titanium surface 40 may, for example, be considered as representing one or more of a portion of the outer housing 12, part or all of the first electrode 20 and/or the second electrode 22 (as seen in FIG. 2). In some cases, for example, the titanium surface 40 may represent part or all of the retrieval feature 39. In some instances, the titanium surface 40 may be considered as representing a portion of any number of different implantable medical devices that include an outer titanium surface over at least a portion thereof.

In some cases, subjecting the titanium surface 40 to a plasma treatment can reduce or eliminate oxidation on the titanium surface 40 and can, in some cases, provide reactive and available hydroxyl groups covalently bonded to individual titanium atoms on or within the titanium surface 40. It will be appreciated that FIG. 3, showing a total of five hydroxylated titanium atoms, is highly schematic.

Figure 4:
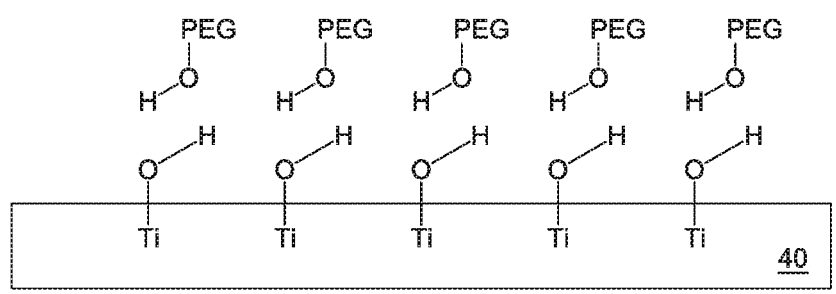
FIG. 4 is a schematic view of the titanium surface of FIG. 3, shown just prior to covalently bonding polyethylene glycol molecules to individual hydroxylated titanium atoms.

After at least some of the titanium atoms at or near an outer surface of the titanium surface 40 have been hydroxylated, a layer of polyethylene glycol may be added. FIG. 4 schematically shows individual polyethylene glycol molecules about to contact individual hydroxylated titanium atoms on or within the titanium surface 40. In some cases, depending on the size and geometry of the titanium surface 40 and/or the implantable medical device including the titanium surface 40 or being represented by the titanium surface 40, the layer of polyethylene glycol may be added simply by dipping or spraying the titanium surface 40 with a liquid polyethylene glycol. As noted, smaller molecular weight polyethylene glycol molecules tend to be liquid at room temperature while larger molecular weight polyethylene glycol molecules tend to be solids at room temperature, but are easily melted. In some cases, the titanium surface 40, after hydroxylation, may be coated with polyethylene glycol molecules within about an hour or so, before the reactive hydroxyl groups are able to react with other moieties.

Figure 5:
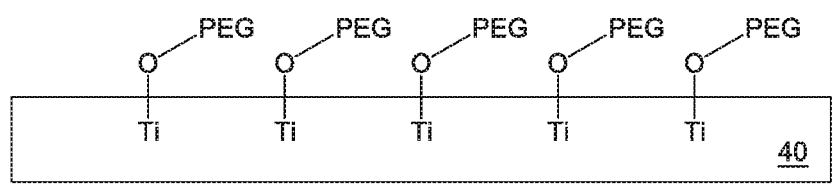
FIG. 5 is a schematic view of the titanium surface of FIG. 3, showing the polyethylene glycol molecules covalently bonded to the individual titanium atoms.

In some cases, as seen in FIG. 5, the terminal hydroxyl group of each polyethylene glycol molecule may react with a hydroxylated titanium atom to form a covalent bond between the oxygen molecule of the hydroxyl group on the titanium atom and the terminal carbon atom of each polyethylene glycol molecule. In some cases, this may be a condensation reaction in which each covalently bonded polyethylene glycol molecule results in the loss of a water molecule. In some cases, the titanium surface 40, bearing the covalently bonded polyethylene glycol molecules, will resist or prevent tissue ingrowth once implanted. In some cases, the polyethylene glycol molecules will form a hydrogel in an aqueous environment such as may be encountered upon implantation within a patient.

Figure 6:
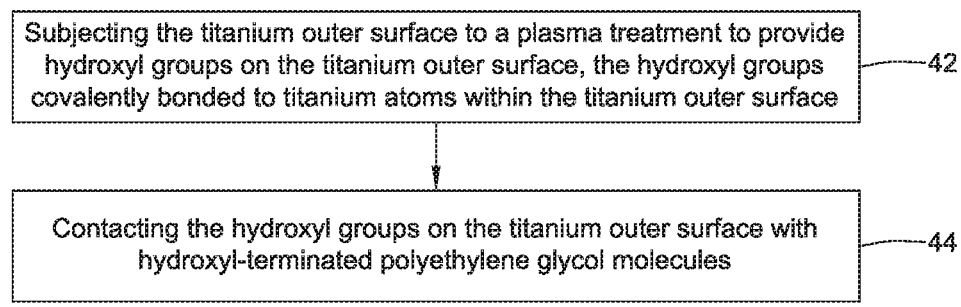
FIG. 6 is a flow diagram showing a method of bonding polyethylene glycol molecules to a titanium surface.

FIG. 6 is a flow diagram providing an illustrative but non-limiting example of instilling tissue growth resistance to at least a portion of an IMD (such as, but not limited to, the IMD 10 shown in FIGS. 1 and 2.) In some cases, the IMD is a leadless cardiac pacemaker (LCP) 1, but this is not required. As generally seen at block 42, the titanium outer surface may be subjected to a plasma treatment to provide hydroxyl groups on the titanium outer surface, the hydroxyl groups covalently bonded to titanium atoms within the titanium outer surface. In some cases, the plasma treatment may be a water plasma treatment. In some cases, the plasma treatment may be an $O_2$ plasma treatment. The hydroxyl groups on the titanium outer surface may be contacted with hydroxyl-terminated polyethylene glycol molecules, as generally seen at block 44.

In some cases, the hydroxyl-terminated polyethylene glycol molecules covalently bond with the hydroxyl groups on the titanium outer surface with a concomitant loss of water molecules. In some instances, contacting the hydroxyl groups on the titanium outer surface with hydroxyl-terminated polyethylene glycol molecules takes place within about one hour or less of subjecting the titanium outer surface to a plasma treatment to provide hydroxyl groups on the titanium outer surface. In some cases, the covalently bonded polyethylene glycol molecules inhibit tissue growth.

EXAMPLES

The disclosure is more particularly illustrated in the following examples, which include experimental information pertaining to forming polyethylene glycol layers on titanium surfaces as well as data illustrating hydrolytic stability and durability.

Example One

In this example, titanium coupons are treated via a water plasma treatment in order to provide reactive hydroxyl groups on the titanium surface and are then coated with melted 3350 PEG. Sufficient 3350 PEG was melted in a beaker set up in a fume hood in order to fully dip all of the coupons. For each set of conditions, two titanium coupons and one glass slide were coated in Parylene to use as test coupons for measuring contact angles.

Procedure:
1. Coupons were wiped clean with IPA (isopropyl alcohol) and lint free wipes.
2. Initial weights were recorded for each coupon.
3. Coupons were subjected to a water plasma treatment at 200 W for the indicated amount of exposure time.
4. Coupons were dipped in melted PEG for 15 seconds and allowed to hang dry.
5. Coupons were again weighed and a post PEG weight was recorded for each.
6. Coupons were placed in oven for indicated period of time.
7. Coupons were again weighed and a final weight was recorded for each.
8. Coupons were placed into baggies filled with PBS (phosphate buffered saline), which were themselves placed into a water bath set at 37° C.
9. Contact angles were periodically measured. Results are in Table Two, below:

TABLE ONE

| | Conditions | |
|---|---|---|
| Sample | Plasma Time (minutes) | Oven Conditions |
| Ti 1 | 1 | 5 min @ 130° C. |
| Ti 2 | 1 | 5 min @ 130° C. |
| GS 3 | 1 | 5 min @ 130° C. |
| Ti 4 | 1 | 5 min @ 130° C., 4 hrs @ 60° C. |
| Ti 5 | 1 | 5 min @ 130° C., 4 hrs @ 60° C. |
| GS 6 | 1 | 5 min @ 130° C., 4 hrs @ 60° C. |
| Ti 7 | 1 | 4 hrs @ 60° C. |
| Ti 8 | 1 | 4 hrs @ 60° C. |
| GS 9 | 1 | 4 hrs @ 60° C. |
| Ti 10 | 5 | 4 hrs @ 60° C. |
| Ti 11 | 5 | 4 hrs @ 60° C. |
| GS 12 | 5 | 4 hrs @ 60° C. |
| Ti 13 | 10 | 4 hrs @ 60° C. |
| Ti 14 | 10 | 4 hrs @ 60° C. |
| GS 15 | 10 | 4 hrs @ 60° C. |

TABLE TWO

| | Results | | | | | |
|---|---|---|---|---|---|---|
| | Contact Angles (Day Number) | | | | | |
| Sample | Day 1 | Day 8 | Day 14 | Day 51 | Day 88 | Control |
| Ti 1 | 16.62 | 12.39 | 14.29 | 11.05 | 19.29 | 86.66 |
| Ti 2 | 17.94 | 15.73 | 13.17 | 12.31 | 13.51 | 88.11 |
| GS 3 | 21.24 | 20.45 | 17.65 | 17.98 | 20.6 | 88.5 |
| Ti 4 | 20.07 | 19.67 | 20.69 | 30.3 | 25.22 | 84.21 |
| Ti 5 | 17.5 | 15.77 | 13.77 | 15.94 | 32.06 | 85.22 |
| GS 6 | 21.54 | 17.58 | 19.3 | 32.05 | 35.48 | 89.14 |
| Ti 7 | 17.28 | 15.48 | 16.93 | 17.08 | 14.73 | 82.78 |
| Ti 8 | 17.77 | 18.84 | 16.9 | 17.81 | 21.21 | 84.31 |
| GS 9 | 19.16 | 19.28 | 19.01 | 14.33 | 27.56 | 87.3 |
| Ti 10 | 15.93 | 12.83 | 10.54 | 8.56 | 10.14 | 85.88 |
| Ti 11 | 13.44 | 13.34 | 14.13 | 10.77 | 10.81 | 86.79 |
| GS 12 | 18.21 | 16.53 | 19.98 | 16.13 | 27.89 | 86.46 |
| Ti 13 | 15.75 | 13.66 | 16.79 | 15.4 | 23.38 | 86.29 |
| Ti 14 | 20.5 | 14.92 | 14.39 | 11.34 | 26.2 | 85.29 |
| GS 15 | 19.16 | 16.1 | 17.24 | 15.6 | 18.4 | 87.94 |

The results indicate that with a water plasma treatment to create exposed hydroxyl groups covalently bonded to titanium atoms in the surface of the titanium coupon, it was possible to add a useful amount of polyethylene glycol to the titanium coupon. The results also indicate an unexpected level of hydrolytic stability given that the polyethylene glycol was bonded directly to the hydroxyl groups on the titanium, without an intervening layer as is commonly used.

Example Two

In this example, titanium coupons are treated via an oxygen plasma treatment in order to provide reactive hydroxyl groups on the titanium surface and are then coated with 400 PEG or melted 3350 PEG. Sufficient 3350 PEG was melted in a beaker set up in a fume hood in order to fully dip all of the coupons.

Procedure:
1. Coupons were wiped clean with IPA (isopropyl alcohol) and lint free wipes.
2. Initial weights were recorded for each coupon.
3. Initial contact angles were measured and recorded
4. Coupons were subjected to an $O_2$ plasma treatment for 5 minutes.
5. Some coupons were dipped in 400 PEG and some were dipped in melted 3350 PEG for 15 seconds and allowed to hang dry.
6. Coupons were again weighed and a post PEG weight was recorded for each.
7. Coupons were placed in oven at 130° C. for five minutes.
8. Coupons were again weighed and a final weight was recorded for each.
9. Coupons were placed into baggies filled with saline, which were themselves placed into a water bath set at 37° C.
10. Contact angles were periodically measured.

TABLE THREE

Weights

| Sample # | PEG type | Initial (g) | Post PEG (g) | Final (g) | PEG added (g) |
|---|---|---|---|---|---|
| 1 | 400 | 0.26926 | 0.31435 | 0.27655 | 0.00729 |
| 2 | 400 | 0.26992 | 0.28836 | 0.27455 | 0.00463 |
| 3 | 400 | 0.27111 | 0.30567 | 0.27739 | 0.00628 |
| 4 | 400 | 0.27033 | 0.31065 | 0.27551 | 0.00518 |
| 5 | 3350 | 0.27287 | 0.34682 | 0.2854 | 0.01253 |
| 6 | 3350 | 0.26977 | 0.3406 | 0.28207 | 0.0123 |
| 7 | 3350 | 0.27158 | 0.34417 | 0.28384 | 0.01226 |
| 8 | 3350 | 0.26836 | 0.34832 | 0.2836 | 0.01524 |

TABLE FOUR

Contact Angles

| Sample # | Day 1 | Day 2 | Day 6 | Day 8 | Day 57 | Control |
|---|---|---|---|---|---|---|
| 1 | n/m | 20.24 | 18.88 | 17.12 | 22.53 | 37.47 |
| 2 | n/m | 19.07 | 20.49 | 22.96 | 29.23 | 37.89 |
| 3 | 8.2 | 14.43 | 14.33 | 15.45 | 16.7 | 38.24 |
| 4 | n/m | 22.58 | 22.34 | 22.49 | 27.23 | 39.7 |
| 5 | 10.83 | 15.87 | 11.69 | 20.78 | 23 | 35.62 |
| 6 | 7.9 | 25.74 | 19.8 | 26.01 | 26.35 | 40.47 |
| 7 | 14.4 | 28.14 | 23.95 | 21.75 | 25.39 | 31.88 |
| 8 | n/m | 30.79 | 24.66 | 28.32 | 27.8 | 32.32 |

The results indicate that with an $O_2$ plasma treatment to create exposed hydroxyl groups covalently bonded to titanium atoms in the surface of the titanium coupon, it was possible to add a useful amount of polyethylene glycol to the titanium coupon. The results also indicate an unexpected level of hydrolytic stability given that the polyethylene glycol was bonded directly to the hydroxyl groups on the titanium, without an intervening layer as is commonly used.

Example Three

In this example, titanium coupons were sterilized and initial contact angle was measured. Once coupons were coated with PEG, they were soaked in saline for one hour in a 37° C. water bath. Contact angle measured after one hour, and again after 105 days. Results are shown in Table Five.

TABLE FIVE

| Coupon | Initial | After Soak | Day 105 |
|---|---|---|---|
| 400 Ti #1 | 13.27 | 25.62 | 37.97 |
| 400 Ti #2 | 15.57 | 29.85 | 27.39 |
| 400 Ti #3 | 11.46 | 22.2 | 25.85 |
| 400 Ti #4 | 20.44 | 49.6 | 28.27 |
| 400 Ti/Parylene #5 | 15.75 | 45.6 | 52.28 |
| 400 Ti/Parylene #6 | 14.81 | 50.88 | 40.33 |
| 3350 Ti #7 | 11.01 | 22.44 | 20.15 |
| 3350 Ti #8 | 9.85 | 24.82 | 35.18 |
| 3350 Ti/Parylene #9 | 8.7 | 29.34 | 43.9 |
| 3350 Ti/Parylene #10 | 9.11 | 32.21 | 54.53 |

The results indicate that with a plasma treatment to create exposed hydroxyl groups covalently bonded to titanium atoms in the surface of the titanium coupon, it was possible to add a useful amount of polyethylene glycol to the titanium coupon. The results also indicate an unexpected level of hydrolytic stability given that the polyethylene glycol was bonded directly to the hydroxyl groups on the titanium, without an intervening layer as is commonly used.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. An implantable medical device (IMD), comprising:
an outer housing having a titanium outer surface;
the titanium outer surface comprising a plurality of titanium atoms;
a tissue growth-inhibiting layer extending over the titanium outer surface;
the tissue growth-inhibiting layer comprising a plurality of polyethylene glycol molecules, at least some of the plurality of polyethylene glycol molecules covalently bonded via an ether bond to one of the plurality of titanium atoms; and
wherein the tissue growth-inhibiting layer is formed by hydroxylating at least some of the plurality of titanium atoms and covalently bonding a plurality of hydroxyl-terminated polyethylene glycol molecules to the hydroxylated titanium atoms with a concomitant loss of water molecules.

2. The IMD of claim 1, wherein the titanium outer surface comprises an electrically active surface.

3. The IMD of claim 2, further comprising an electrically insulating layer disposed over a first portion of the outer housing and the electrically active surface comprises a second portion of the outer housing without the electrically insulating layer.

4. The IMD of claim 2, wherein the tissue growth-inhibiting layer extends over at least a portion of the electrically active surface.

5. The IMD of claim 1, wherein the titanium outer surface comprises a retrieval feature.

6. The IMD of claim 5, wherein the tissue growth-inhibiting layer extends over at least a portion of the retrieval feature.

7. The IMD of claim 1, wherein the tissue growth-inhibiting layer exhibits hydrolytic stability in the presence of water.

8. The IMD of claim 1, wherein the tissue growth-inhibiting layer is water-swellable.

9. A leadless cardiac pacemaker (LCP) configured for removal after having been chronically implanted, the LCP comprising:
- an outer housing extending from a proximal end to a distal end;
- a fixation element extending distally from the distal end;
- a retrieval feature extending proximally from the proximal end;
- at least a portion of the LCP including a titanium outer surface; and
- a tissue growth-inhibiting layer extending over at least a portion of the titanium outer surface, the tissue growth-inhibiting layer comprising a plurality of polyethylene glycol molecules each covalently bonded to titanium atoms within the titanium outer surface.

10. The LCP of claim 9, further comprising a titanium electrode disposed relative to the outer housing.

11. The LCP of claim 9, wherein the tissue growth-inhibiting layer extends over at least a portion of the titanium electrode.

12. The LCP of claim 9, wherein the retrieval feature comprises the titanium outer surface, and the tissue growth-inhibiting layer extends over at least a portion of the retrieval feature.

13. The LCP of claim 9, wherein the outer housing comprises the titanium outer surface, and the tissue growth-inhibiting layer extends over at least a portion of the outer housing.

14. A method of instilling tissue growth resistance to at least a portion of an implantable medical device (IMD), the IMD having a titanium outer surface, the method comprising:
- subjecting the titanium outer surface to a plasma treatment to provide hydroxyl groups on the titanium outer surface, the hydroxyl groups covalently bonded to titanium atoms within the titanium outer surface;
- contacting the hydroxyl groups on the titanium outer surface with hydroxyl-terminated polyethylene glycol molecules; and
- wherein the hydroxyl-terminated polyethylene glycol molecules covalently bond with the hydroxyl groups on the titanium outer surface with a concomitant loss of water molecules.

15. The method of claim 14, wherein contacting the hydroxyl groups on the titanium outer surface with hydroxyl-terminated polyethylene glycol molecules takes place within about one hour or less of subjecting the titanium outer surface to a plasma treatment to provide hydroxyl groups on the titanium outer surface.

16. The method of claim 14, wherein subjecting the titanium outer surface to a plasma treatment to provide hydroxyl groups on the titanium outer surface comprises a water plasma treatment.

17. The method of claim 14, wherein subjecting the titanium outer surface to a plasma treatment to provide hydroxyl groups on the titanium outer surface comprises an $O_2$ plasma treatment.

18. The method of claim 14, wherein the IMD is a leadless cardiac pacemaker (LCP).

19. The method of claim 14, wherein the covalently bonded polyethylene glycol molecules inhibit tissue growth.

* * * * *